(12) United States Patent
Madsen (10) Patent No.: US 12,290,624 B2
(45) Date of Patent: May 6, 2025

(54) SYSTEM AND METHOD FOR IRRADIATING BIOLOGICAL FLUIDS

(71) Applicant: Fenwal, Inc., Lake Zurich, IL (US)

(72) Inventor: James Madsen, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/945,411

(22) Filed: Jul. 31, 2020

(65) Prior Publication Data

US 2021/0038802 A1   Feb. 11, 2021

Related U.S. Application Data

(60) Provisional application No. 62/884,780, filed on Aug. 9, 2019.

(51) Int. Cl.
*A61M 1/36* (2006.01)
*A61M 1/30* (2006.01)

(52) U.S. Cl.
CPC ........ *A61M 1/3683* (2014.02); *A61M 1/3622* (2022.05); *A61M 1/3693* (2013.01); *A61M 1/303* (2014.02); *A61M 2205/053* (2013.01); *A61M 2205/3331* (2013.01); *A61M 2205/50* (2013.01); *A61M 2205/587* (2013.01)

(58) Field of Classification Search
CPC .. A61M 1/303; A61M 1/3681; A61M 1/3683; A61M 1/3693; A61M 2205/053; A61M 2205/103; A61M 2205/3331; A61M 2205/50; A61M 2205/587; A61M 2209/084

See application file for complete search history.

(56) References Cited

U.S. PATENT DOCUMENTS

| | | | |
|---|---|---|---|
| 5,133,932 A | * | 7/1992 | Gunn .................. A61L 2/10 210/243 |
| 5,316,667 A | | 5/1994 | Brown et al. |
| 5,360,542 A | | 11/1994 | Williamson, IV et al. |
| 5,868,696 A | | 2/1999 | Giesler et al. |
| 6,312,593 B1 | | 11/2001 | Petrie |
| 6,369,394 B1 | * | 4/2002 | Lee ..................... B01F 31/55 250/455.11 |

(Continued)

FOREIGN PATENT DOCUMENTS

| | | |
|---|---|---|
| EP | 1693072 | 8/2006 |
| WO | WO 01/74407 | 10/2001 |

OTHER PUBLICATIONS

Extended European Search Report, counterpart EP App. No. 20189833 (Feb. 10, 2021) (7 pages).

*Primary Examiner* — Dirk R Bass
(74) *Attorney, Agent, or Firm* — Cook Alex Ltd.

(57) ABSTRACT

An irradiation device includes a processing container including a first chamber, a second chamber and at least one narrow passage in fluid communication at a first end with the first chamber and at a second end with the second chamber, and a rotatable table on which the processing container is mounted, the table having a first state wherein the first chamber is disposed at a higher elevation than the second chamber, and a second state wherein the second chamber is disposed at a higher elevation than the first chamber. The irradiation device also includes ultraviolet (UV) light source disposed proximate to the narrow passage and configured to irradiate fluid passing through the narrow passage.

18 Claims, 8 Drawing Sheets

(56) References Cited

U.S. PATENT DOCUMENTS

| | | |
|---|---|---|
| 6,908,460 B2 | 6/2005 | DiStefano |
| 7,433,030 B2 | 10/2008 | Waldo et al. |
| 7,753,869 B2 | 7/2010 | Davidner et al. |
| 9,533,089 B2 | 1/2017 | Min et al. |
| 2002/0138066 A1* | 9/2002 | Manica ................ A61J 1/2093 |
| | | 604/522 |
| 2003/0045868 A1 | 3/2003 | DiStefano |
| 2003/0214874 A1* | 11/2003 | Hlavinka ................ B01F 33/05 |
| | | 366/214 |

* cited by examiner

SYSTEM AND METHOD FOR IRRADIATING BIOLOGICAL FLUIDS

CROSS-REFERENCE TO RELATED APPLICAITONS

This application claims the benefit of U.S. Provisional Patent App. No. 62/884,780, filed Aug. 9, 2019, which is expressly incorporated herein by reference in its entirety.

TECHNICAL FIELD

The present disclosure is generally directed to a system and method for processing a biological fluid, and in particular a biological fluid processing system or method where the processing includes irradiation of the biological fluid.

BACKGROUND

Biological fluid processing systems may be configured to process biological fluid, such as may be drawn from a patient, to provide a product that may be returned to the patient, for example. These processing systems may include a reusable processor or separator, as well as a disposable fluid circuit or set. According to certain systems, the circuit or set may be connected to the patient to exchange fluids with the patient. The set may also be connected to various containers that include other fluids, such as wash solutions and the like.

During the processing, the biological fluid may be combined with a photoactive compound, and then the fluid may be exposed to ultraviolet (UV) light. For example, the fluid may contain mononuclear cells (MNC), and may be combined with 8-methoxypsoralen ("8-MOP"). It is believed that the combination of 8-MOP and the photoactivation causes apoptosis, or programmed cell death, of T-cells.

At present, the MNC is collected in a long flexible container or bag that is disposed in a photoactivation device, such as is illustrated in U.S. Pat. No. 7,433,030. These long flexible containers are irradiated using long UV bulbs, which bulbs are disposed parallel to the container, typically both above and below the container. Further, the length of the UV bulbs and the length of the flexible container is approximately the same. As a result of the use of large numbers of long UV bulbs, these photoactivation devices may make high power demands, resulting in added expense.

The photoactivation devices typically also include some form of mixing mechanism to mix the fluid in the container, because the cells nearer the surface of the container, and thus nearer the UV bulbs, receive a higher dose of radiation than cells in the center of the container. In addition, care is required to ensure an even thickness to reduce the likelihood of formation of hot and cold regions in the container during photoactivation. Because of the issues with conventional technology, and particular those issues relating to maintaining an even fluid thickness, the volume of biological fluid treated using such technology may be limited.

SUMMARY

In an aspect of the disclosure, an irradiation device includes a processing container including a first chamber, a second chamber and at least one narrow passage in fluid communication at a first end with the first chamber and at a second end with the second chamber, and a rotatable table on which the processing container is mounted, the table having a first state wherein the first chamber is disposed at a higher elevation than the second chamber, and a second state wherein the second chamber is disposed at a higher elevation than the first chamber. The irradiation device also includes ultraviolet (UV) light source disposed proximate to the narrow passage and configured to irradiate fluid passing through the narrow passage.

DETAILED DESCRIPTION

A detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
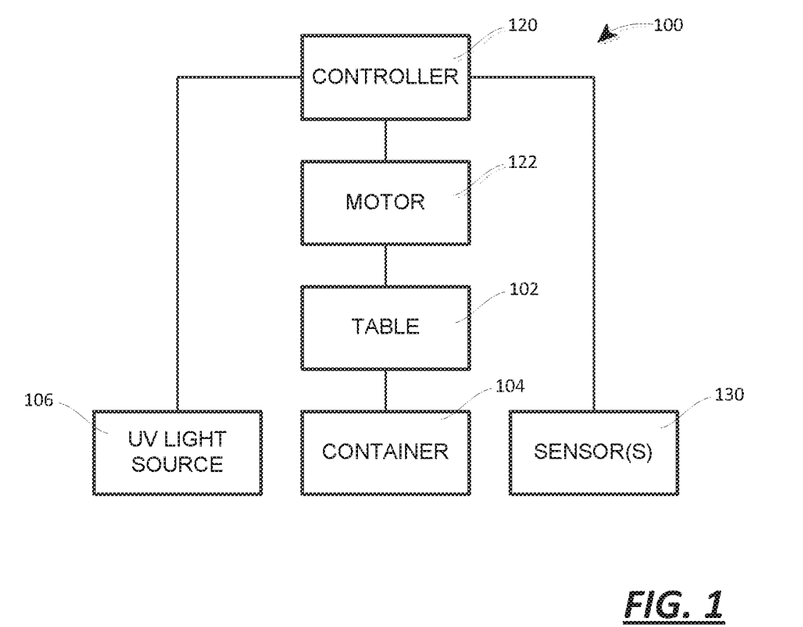
FIG. 1 is a block diagram of an embodiment of an irradiation device.
Figure 2:
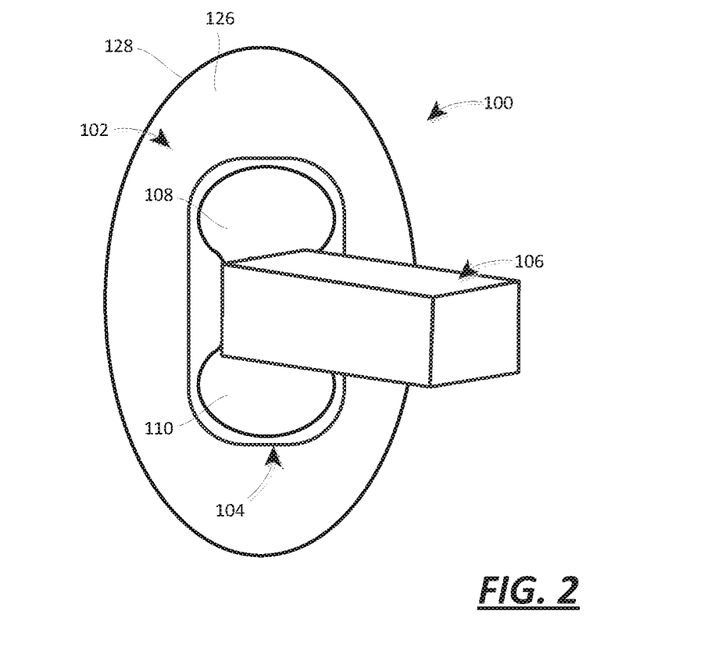
FIGS. 2 and 3 are perspective views of an irradiation device such as is illustrated in FIG. 1.
Figure 3:
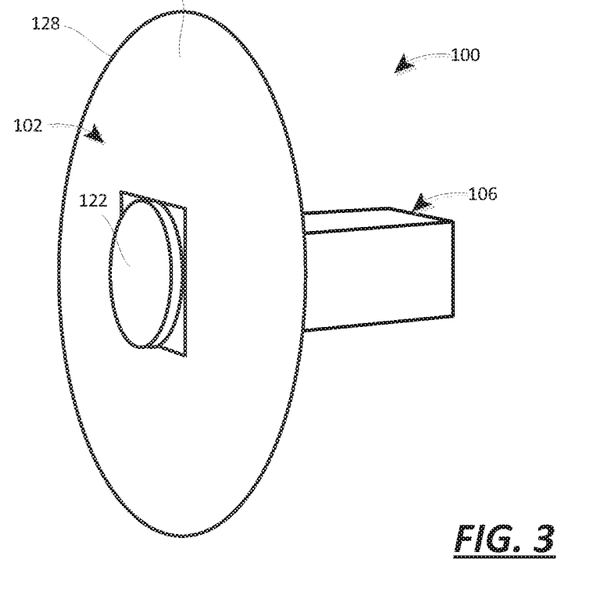

As illustrated in FIGS. 1-3, an irradiation device 100 includes rotatable table 102 on which a processing container 104 is mounted, The irradiation device 100 also includes an ultraviolet (UV) light source 106 that is used to irradiate fluid in the processing container 104.

Figure 4:
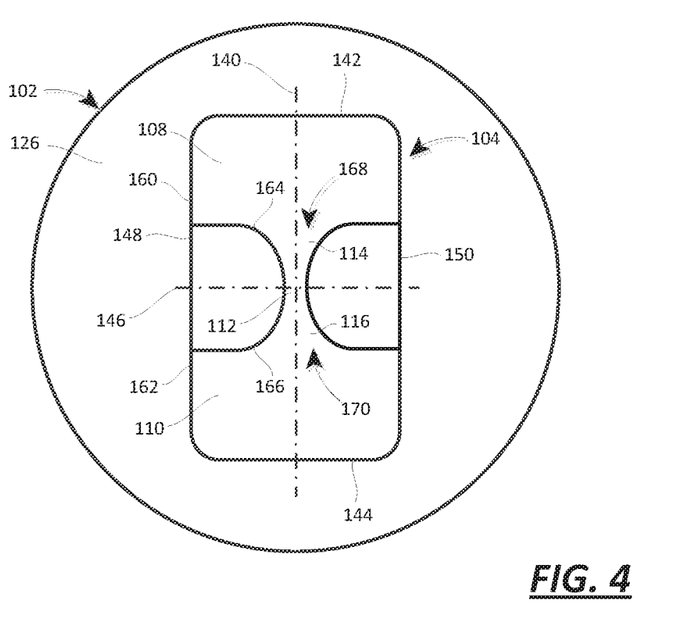
FIG. 4 is a plan view of an embodiment of a processing container for use in the irradiation device of FIG. 1, mounted on a circular table.
Figure 5:
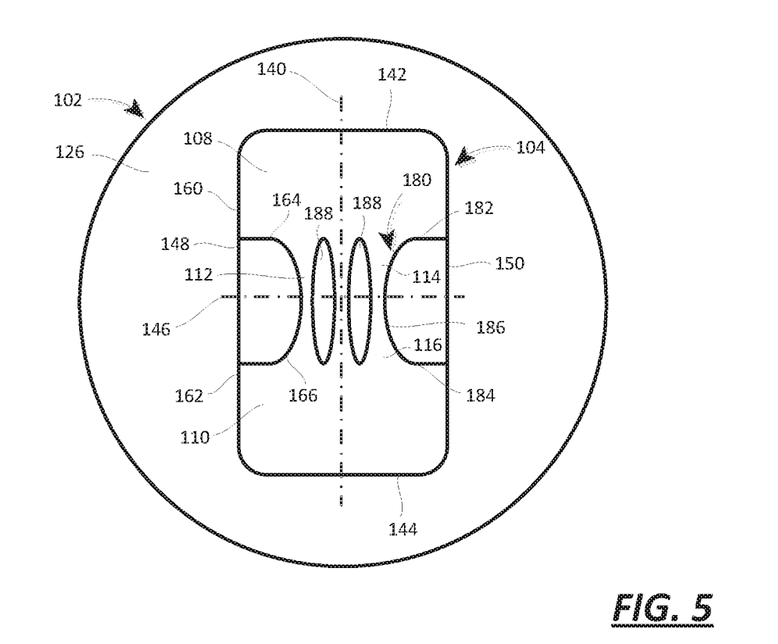
FIG. 5 is a plan view of another embodiment of a processing container for use in the irradiation device of FIG. 1, mounted on a circular table.
Figure 6:
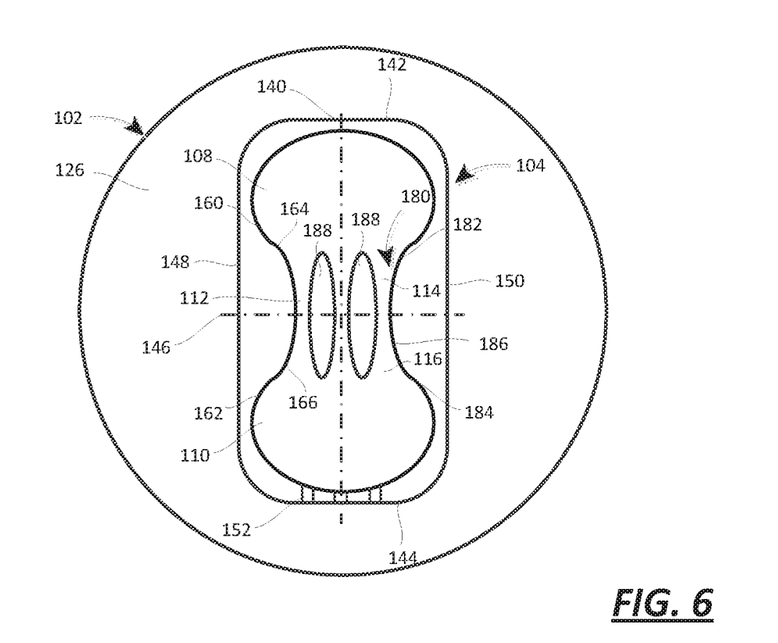
FIG. 6 is a plan view of a further embodiment of a processing container for use in the irradiation device of FIG. 1, mounted on a circular table.

As illustrated in FIGS. 4-6, the processing container 104 includes a first chamber 108, a second chamber 110 and at least one narrow passage 112. The at least one narrow passage 112 (a single passage 112 as illustrated in FIG. 4 and a plurality of passages 112 as illustrated in FIGS. 5 and 6)

is in fluid communication at a first end 114 with the first chamber 108 and at a second end 116 with the second chamber 110.

As illustrated in FIGS. 7-10, the table 102 has a first state (or position, such as an angular position) wherein the first chamber 108 is disposed at a higher elevation than the second chamber 110, and a second state wherein the second chamber 110 is disposed at a higher elevation than the first chamber 108. As Illustrated in FIGS. 2 and 3 and schematically in FIGS. 7-10, the UV light source 106 is disposed proximate to the at least one narrow passage 112 and configured to irradiate fluid passing through the at least one narrow passage 112. In particular, the UV light source 106 is aligned with the passages 112, and in the illustrated embodiments, the light source 106 is aligned with the passages 112 so as to irradiate only fluid with the passages 112 and not fluid within the chambers 108, 110.

Figure 7:
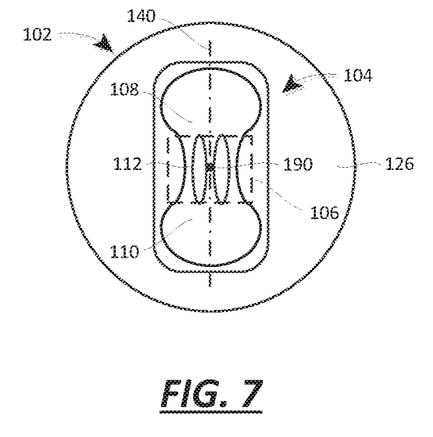
FIGS. 7-10 are schematic drawings of the processing container and table of FIG. 6 during the operation of the device according to an embodiment of a method of irradiating a biological fluid.

According to a method of operation, the processing container 104 is mounted on the table 102, for example through the use of one or more fasteners attached to the table, which fasteners may be disposed through openings formed in the container 104 or may grip parts of the container 104. The container 104 may be oriented initially as illustrated in FIG. 7, with the first chamber 108 disposed at a higher elevation (or above) the second chamber 110 (i.e., the first state). In this state, the fluid to be processed is in the second chamber 110. The table 102 is then rotated from the first state to the second state, with the second chamber 110 disposed at a higher elevation (or above) the first chamber 108.

As the table 102 is moved from the first state to the second state, the fluid in the second chamber 110 starts to move in the second chamber 110, which may cause mixing of the contents in the second chamber 110, particularly where more than one component is present. Further, the fluid in the second chamber 110 may at least start to enter the narrow passages 112, depending on the geometry of the second chamber 110 and the orientation of the container 104. Once the table 102 is in the second state, the fluid should enter all of the passages 112 and move under the force of gravity from the second chamber 110 to the first chamber 108.

At least as the fluid moves from the second chamber 110 to the first chamber 108, the UV light source 106 is activated. According to certain embodiments, the UV light source 106 is activated throughout the process. As illustrated in FIGS. 2, 3, and 7-10 the UV light source 106 need not move with the table 102, but may be disposed separately from the table 102, such that the table 102 and the container 104 move (rotate) relative to the UV light source.

Figure 10:
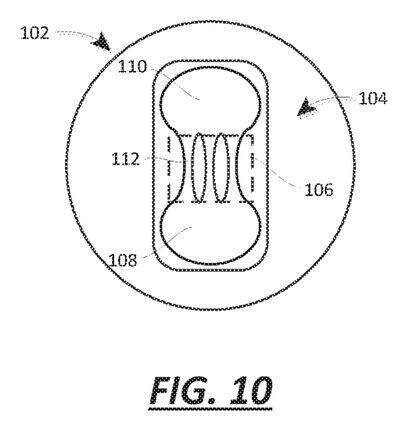

As illustrated in FIG. 10, the fluid has moved from the second chamber 110 to the first chamber 108. At this point, the device 100 is ready to move the table 102 between the second state and the first state, so as to cause the fluid to move from the first chamber 108 to the second chamber 110.

Having thus explained the general structure and operation of the device 100 with reference to FIGS. 1-10, the details of the structure and operation are now discussed, first with reference to FIG. 1.

The block diagram of FIG. 1 illustrates an embodiment of the device 100 wherein the operation of the device 100 has been automated. To this end, the device 100 includes a controller 120. The controller 120 may be may include a microprocessor (which, in fact may include multiple physical and/or virtual processors). According to other embodiments, the controller 120 may include one or more electrical circuits designed to carry out the actions described herein. In fact, the controller 120 may include a microprocessor and other circuits or circuitry. In addition, the controller 120 may include one or more memories. The instructions by which the microprocessor is programmed may be stored on the memory or memories associated with the microprocessor, which memory/memories may include one or more tangible non-transitory computer readable memories, having computer executable instructions stored thereon, which when executed by the microprocessor, may cause the microprocessors to carry out one or more actions or methods as described below.

The controller 120 is coupled to the UV light source 106. The controller 120 may be configured to activate the UV light source 106 to irradiate the narrow passage(s) 112 throughout the operation of the device 100, for example as long as a container 104 is mounted to or on the table 102. According to other embodiments, the controller 120 may be configured to activate the UV light source 106 to irradiate the narrow passage(s) 112 only when the fluid is flowing through the passage(s) 112. For example, the controller 120 may activate the UV light source 106 only when the table is in the second state after having previously been in the first state, and to deactivate the UV light source 106 when all or almost all (e.g., 95%, 98% or 99%) of the fluid has moved from one chamber to the other chamber.

The UV light source 106 may include one or more light emitting diodes that emit radiation in the UV spectrum. According to an embodiment, the UV light source 106 includes a plurality of UV light emitting diodes (LED) arranged in an array. According to such an embodiment, the UV LED array may be, for example, a one dimensional array (e.g. disposed along a line) or a two dimensional array (e.g., disposed over an area having length and width). According to other embodiments, other light sources, such as bulbs, may be used.

The light source 106 may be disposed proximate to the passage(s) 112 as illustrated in FIG. 2 and schematically in FIGS. 7-10 with all components of the light source 106 disposed proximate to the passage(s) 112. The light source 106 may be disposed proximate to the passage(s) 112 by using one or more optical conduits (such as optic fibers or fiber optic cables) with a first end disposed proximate to the passage(s) 112 and a second end disposed proximate to the LED array, the LED array being disposed remotely from the passage(s) 112. Either embodiment is referred to herein as having the light source disposed proximate to the passage(s) 112.

The controller 120 may also be coupled to a motor 122 that is attached to the table 102, for example on a surface 124 of the table 102 opposite a surface 126 of the table 102 to which or on which the processing container 104 is mounted. Compare FIGS. 2 and 3. It is not necessary that the motor 122 be mounted on a surface of the table 102; instead, the motor 122 may be mounted to the side of the table 102 and may interact with an edge 128 of the table to cause the table 102 to rotate. Further, the table 102 may be mounted on a shaft, and the motor 122 may be mounted separately from the table 102 and the shaft, and may be coupled to the shaft (e.g., through the use of a belt and sprocket) to cause the table 102 to rotate.

Figure 8:
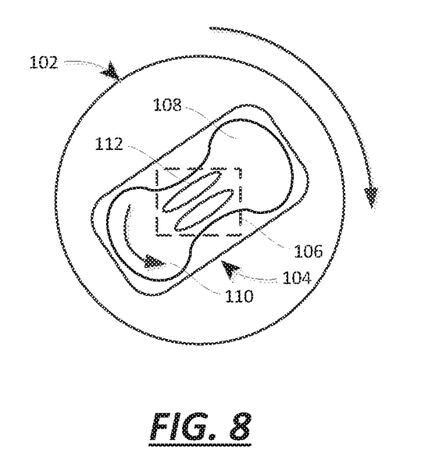
Figure 9:
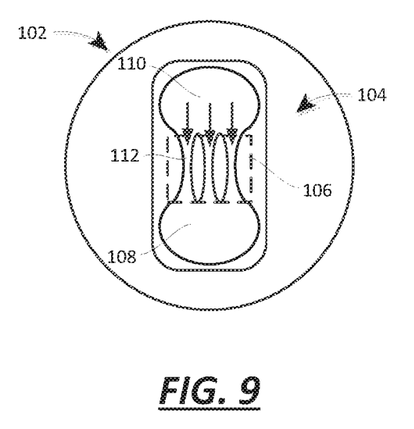

The motor 122 may be capable of operation only in a single direction, such as in the clockwise direction as illustrated in FIG. 8. If so, then the controller 120 would activate the motor 122 to move the table from the first state to the second state, and from the second state to the first state, in the clockwise direction. According to another embodiment, the motor 122 may be capable of bi-directional operation, or clockwise and counterclockwise directions. If so, then the controller 120 may activate the motor 122 to move the table from the first state to the second state in the clockwise direction, for example, and then from the second state to the first state in the counterclockwise direction.

The controller 120 may also be coupled to one or more sensors 130 (see FIG. 1). The sensors 130 may be used to determine the orientation of the table 102, and of the container 104 as a consequence. The sensors 130 may be used to determine if all or almost all of the fluid has moved from one chamber to the other chamber. The sensors 130 may be used to determine the intensity of the radiation emitted by the light source 106, or the temperature of the fluid in the container 104. The sensors 130 may include optical sensors that are disposed on one or both sides of the container 104 (such as may be used to determine if there is fluid remaining in one of the chambers), or the sensors may interact with a material disposed about the edge 128 of the table (such as may be used to determine the orientation of the table 102 on a relative or absolute basis).

As illustrated in FIGS. 4-6, the shape of the container 104, and of the chambers 108, 110, may vary. Likewise, the shape of the passage(s) 112 may vary between different embodiments. Several embodiments have been provided in FIGS. 4-6 to illustrate different aspects of the container 104.

As a general comment applicable to the illustrated embodiments, the container 104 may be made of a material that is transparent, or at least translucent to light of the wavelength produced by the light source (e.g., UV light). According to the illustrated embodiments, the container 104 is also made of a flexible material, such that the container 104 may be bent without damage.

As a further general comment, the container 104 has a longitudinal axis 140 that extends between opposite first and second ends 142, 144 of the container 104. The chambers 108, 110 are disposed along the longitudinal axis 140; as illustrated, the chambers 108, 110 may also be referred to as aligned with the longitudinal axis 140 in that they are disposed along the longitudinal axis. The passage or passages 112 are also aligned with the longitudinal axis 140, with the first end(s) 114 of the passage(s) 112 closer to the first end 142 of the container 104 and the second end(s) 116 of the passage(s) 112 closer to the second end 144 of the container 104. Again, in consideration of the symmetry of the passage or passages 112 about the longitudinal axis 140, the passage(s) 112 may be described as aligned with the longitudinal axis 140.

The container 104 also has a lateral axis 146 that extends between opposite first and second sides 148, 150 of the container 104. The lateral axis 146 is orthogonal to the longitudinal axis 148. To the extent a dimension of the chamber 108, 110 or the passage 112 in the longitudinal direction may be referred to as the length of the chamber 108, 110 or passage 112, a dimension of the chamber 108, 110 or the passage 112 in the lateral direction may be referred to as the width of the chamber 108, 110 or passage 112.

It will be recognized that the passage 112 is narrow in the sense that the width of the passage 112 is significantly smaller than the width of the first and second chambers 108, 110. As illustrated, even in those embodiments that include a plurality of passages 112, each of the individual passages 112 in the plurality of passages 112 is significantly smaller than the width of the first and second chambers. For example, the width of the passage 112 may be less than 10% of the width of the chamber 108 or the chamber 110. According to other embodiments, the width of the passage 112 may be, e.g., 5% or 15% of the width of the chamber 108, or the chamber 110.

In addition, although not illustrated in each of the embodiments, the container 104 may have one or more ports 152 attached thereto or formed therewith. See FIG. 6. The ports 152 may be couplable to other fluid circuits to permit biological fluid to be directed into the container 104 (chamber 108 or 110). The ports 152 may also be used to remove materials from the container 104.

Returning to FIG. 4, this embodiment of the container 104 includes a first chamber 108 and a second chamber 110. The container 104 also includes a single narrow passage 112 that is in fluid communication with the first chamber 108 at the first end 114 and with the second chamber 110 at the second end 116.

Each of the first and second chambers 108, 110 is defined by a wall or walls 160, 162. In particular, the wall 160 (or region 160 of combined wall 160, 162) defines the first chamber 108 and the wall 162 (or region 162 of the combined wall 160, 162) defines the second chamber 110. It may also be said that the wall 160 defines the first chamber 108, while the wall 162 defines the second chamber 110. The wall 160, 162 may be a structure separate from a front sheet and a back sheet of the container 104, or the walls 160, 162 may be defined by joining the front and back sheets together to form the wall 160, 162.

The wall 160, 162 may have at least a curved section 164, 166 that defines a volume 168, 170. In FIG. 4, both of the curved sections 164, 166 taper to define the narrow passage 112. The curved nature of the sections 164, 166 is believed to assist in the transfer of the fluid between the chambers 108, 110 by limiting the obstacles to flow between the chambers 108, 110 and the passage 112.

Turning now to FIG. 5, this embodiment of the container 104 also includes a first chamber 108 and a second chamber 110. The container 104 includes a plurality of narrow passages 112 that are in fluid communication with the first chamber at first ends 114 and with the second chamber 110 at second ends 116.

To define the narrow passages 112, the container 104 may include a passage 180 in fluid communication with the first chamber 108 at a first end 182 and the second chamber 110 at the second end 184, the passage 180 having a passage wall 186. The container 104 also includes one or more baffles 188 disposed in the passage 180 to define the plurality of narrow passages 112 between the one or more baffles 188 and the passage wall 186. In fact, the embodiment of FIG. 5 includes a plurality of baffles 188, and at least one of the narrow passages 112 is defined between two of the plurality of baffles 188.

Turning to the embodiment of FIG. 6, this embodiment this embodiment of the container 104 also includes a first chamber 108 and a second chamber 110. The container 104 includes a plurality of narrow passages 112 that are in fluid communication with the first chamber at first ends 114 and with the second chamber 110 at second ends 116.

The wall(s) 160, 162 are entirely curved. As such the wall(s) 160, 162 define a volume 168, 170 that incudes the entire chamber 108, 110.

To define the narrow passages 112, the container 104 may include a passage 180 in fluid communication with the first chamber 108 at a first end 182 and the second chamber 110 at the second end 184, the passage 180 having a passage wall 186. The container 104 also includes one or more baffles 188 disposed in the passage 180 to define the plurality of narrow passages 112 between the one or more baffles 188 and the passage wall 186. In fact, the embodiment of FIG. 5 includes a plurality of baffles 188, and at least one of the narrow passages 112 is defined between two of the plurality of baffles 188.

As mentioned above, the first chamber 108 and the second chamber 110 are disposed along a longitudinal axis 140 of the processing container 104. As will be recognized relative to FIGS. 7-10, the table 102 is rotatable about a table axis 190 that is transverse to the longitudinal axis 140 (see FIG. 7), and thus extends into and out of the page of the drawings. As illustrated, the table axis 190 is orthogonal to the longitudinal axis 140.

More particularly, the table 102 has the table surface 126 on which or to which the processing chamber 104 is attached, and the table axis 190 is orthogonal to the table surface 126. Consequently, the table 102 revolves about the table axis 190 to move the first and second chambers 108, 110 between the first and second states as illustrated in FIGS. 7-10. As mentioned above, and as illustrated in FIG. 3, the device 100 may include motor 122 to rotate the table 102 about the table axis 190.

It will be recognized that the table could alternatively rotate about a table axis that is orthogonal to the longitudinal axis 140 of the container (e.g., parallel or coincident with the lateral axis 146), but not orthogonal to the surface 126. This alternate table axis instead would lie in the plane of the table 102 or parallel thereto. By revolving the table 102 about this axis, it would be possible to achieve a first state wherein the first chamber 108 is above the second chamber 110, and a second state wherein the second chamber 110 is above the first chamber 108. According to such an embodiment, it may be more efficient to have the UV light source 106 mounted to the table 102 as well, with opposing surfaces of the table 102 and the light source 106 spaced for the introduction of the container 104.

Figure 11:
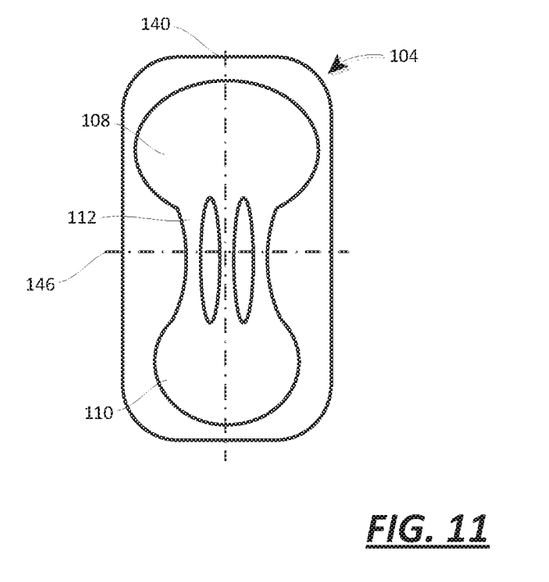
FIG. 11 is a plan view of a still further embodiment of a processing container for use in the irradiation device of FIG. 1.
Figure 12:
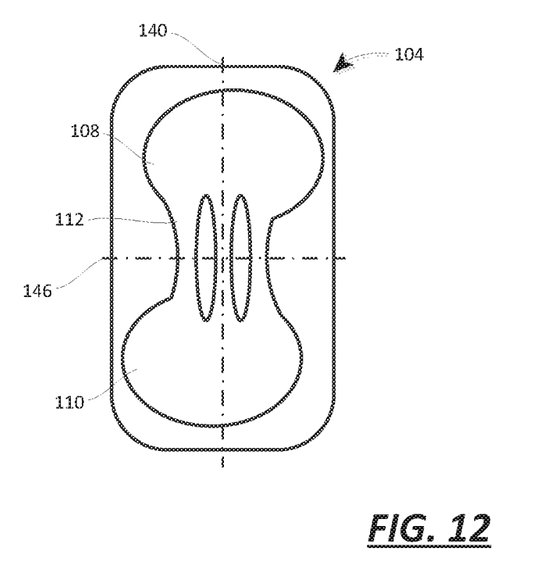
FIG. 12 is a plan view of a yet another embodiment of a processing container for use in the irradiation device of FIG. 1.

Further variants of the processing container 104 are illustrated in FIGS. 11 and 12. These variants include features that could be used separately, or in combination with each other or with the features of the other embodiments of the processing container 104 described above in FIGS. 1-10. Consequently, it will be recognized that the illustrations of FIGS. 11 and 12 are provided by way of explanation, not by way of limitation.

The processing container 104 of FIG. 11 illustrates an embodiment where in the first chamber 108 and the second chamber 110 have different sizes, and may also have different shapes and volumes. As illustrated, the first chamber 108 has larger dimensions in the direction of the longitudinal axis 140 and the lateral axis 146 (i.e., length and width). It will be recognized that according to other embodiments, either dimension (length or width) may be different between the chambers 108, 110, while the other dimension is the same. If the dimension of the chambers 108, 110 into the plane of the page (thickness) is the same, then the difference in the dimensions along the axis 140, 146 (length or width) will result in a difference in volume between the chambers 108, 110. It will be recognized that according other embodiments, it may be possible to vary the dimensions of the chambers 108, 110 (length, width, and thickness) while maintaining the same volume for each of the chambers 108, 110. As also illustrated in FIG. 11, the shape of the chambers 108, 110 may vary, with the chamber 108 being more oval in shape that the chamber 110, for example; greater differences in shape (e.g., one with curved sides vs. one with straight sides) may also be possible.

In the processing container 104 of FIG. 11, the container 104 is symmetrical about the longitudinal axis 140, but is not symmetrical about the lateral axis 146 by virtue of the fact that the chambers 108, 110 are of a different size (having different dimensions). It is also possible for the container 104 not to be symmetrical about either axis 140, 146. The processing container 104 of FIG. 12 illustrates such an embodiment where the container 104 is not symmetrical about either axis 140, 146. Instead, the chambers 108, 110 have centers that are offset from the longitudinal axis 140 in opposite directions.

It will be recognized that the variations in the container 104, such as represented in FIGS. 11 and 12, can be used, for example, to vary the motion of the fluid between the chambers 108, 110 as the container 104 is changed in orientation, for example as illustrated in FIGS. 7-10. The inner surfaces of the chambers 108, 110 and the passage(s) 112 may also be varied (e.g., textured) to vary the motion of the fluid. Variations in the motion of the fluid as it transfers between the chambers 108, 110 may further influence the mixing of the fluid within the chambers 108, 110 and in the passages 112. The variations in the container 114 may also be used to facilitate the transfer of the fluid between the chambers 108, 110, and between the chambers 108, 110 and the passages 112, such as in the embodiment of the processing container 104 in FIG. 12, by providing a smoother transition between the chamber 108, 110 and the passages 112.

Figure 13:
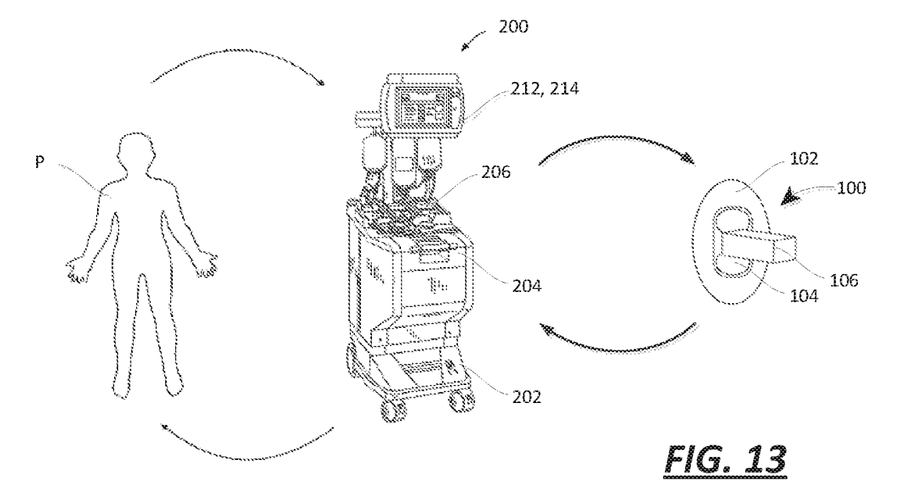
FIG. 13 a schematic diagram of an embodiment of a medical system including a reusable apparatus, a disposable processing set or fluid circuit mounted on or to the reusable apparatus, and an irradiation device.
Figure 14:
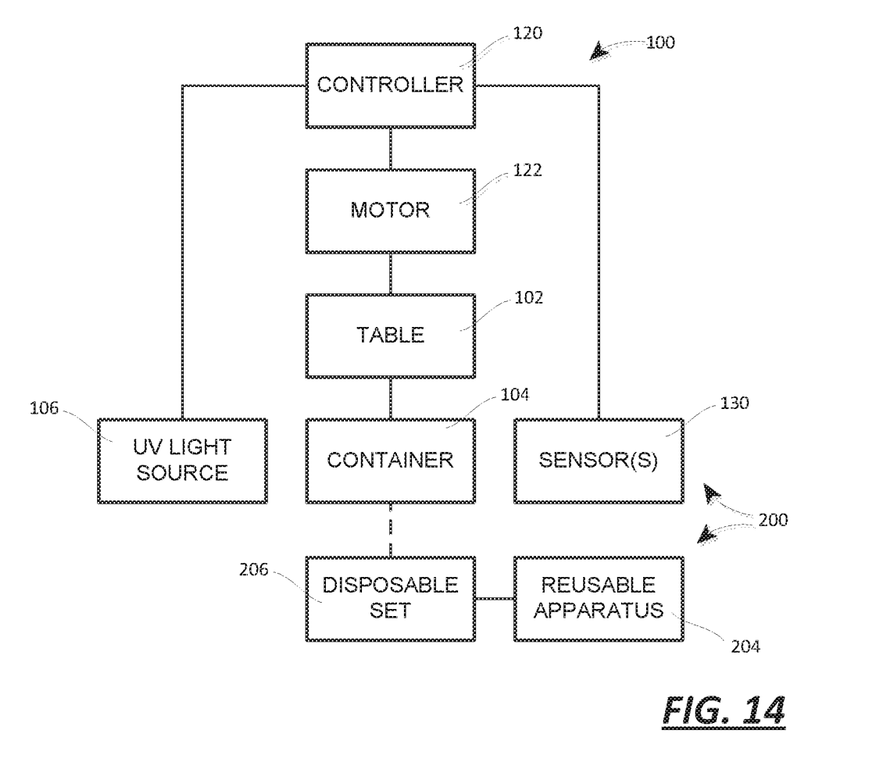
FIG. 14 is a block diagram of the medical system according to FIG. 13.

While the irradiation device 100 may be used independent and apart from equipment that takes a biological fluid and separates it into components, the irradiation device 100 may also be used as part of a system for processing a biological fluid. As illustrated in FIGS. 13 and 14, such a system 200 may include a cell separator 202 configured to separate a biological fluid into at least two streams of cell components, using for example a centrifugal separator, spinning membrane, etc. Further, the system 200 may include an irradiation device 100, including a rotatable table 102, a processing container 104, and a (UV) light source 106. Such a system 200 could be used to perform a variety of photo-treatments, such as extracorporeal photopheresis (ECP) as simply one example.

The processing container 104 of the irradiation device 100 may be couplable to the cell separator 202 to receive the cell components of at least one of the at least two streams. The processing container also may include a first chamber 108, a second chamber 110 and at least one narrow passage 112 in fluid communication at a first end 114 with the first chamber 108 and at a second end 114 with the second chamber 110, as illustrated in FIGS. 1-12.

The processing container 104 of the irradiation device 100 of such a system 200 may be mounted on or to the table 102. The table 102 may have a first state wherein the first chamber 108 is disposed at a higher elevation than the second chamber 110, and a second state wherein the second chamber 110 is disposed at a higher elevation than the first chamber 108. Further, the (UV) light source 106 may be disposed proximate to the narrow passage 112 and configured to irradiate fluid passing through the narrow passage 112

All of the discussion regarding the various embodiments of the irradiation device 100 may apply to the irradiation device 100 included as part of the system 200, as indicated generally in FIG. 14 through the inclusion of the controller 120, motor 122, and sensors 130. As also indicated in FIG. 14, the cell separator 202 may include a reusable apparatus 204 and a disposable fluid circuit 206 mounted to or on the reusable apparatus 204, the fluid circuit 206 couplable to the processing container 104. According to certain embodiments, the processing container 104 is detachable from the fluid circuit 206.

Figure 15:
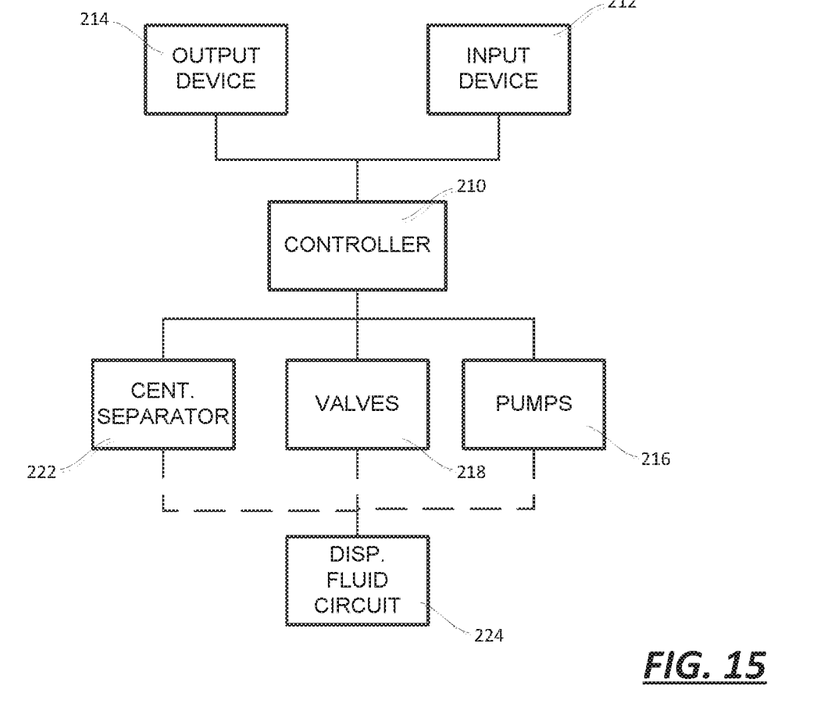
FIG. 15 is a block diagram of an embodiment of a reusable apparatus and a disposable set as may be part of the medical system according to FIG. 13.
Figure 16:
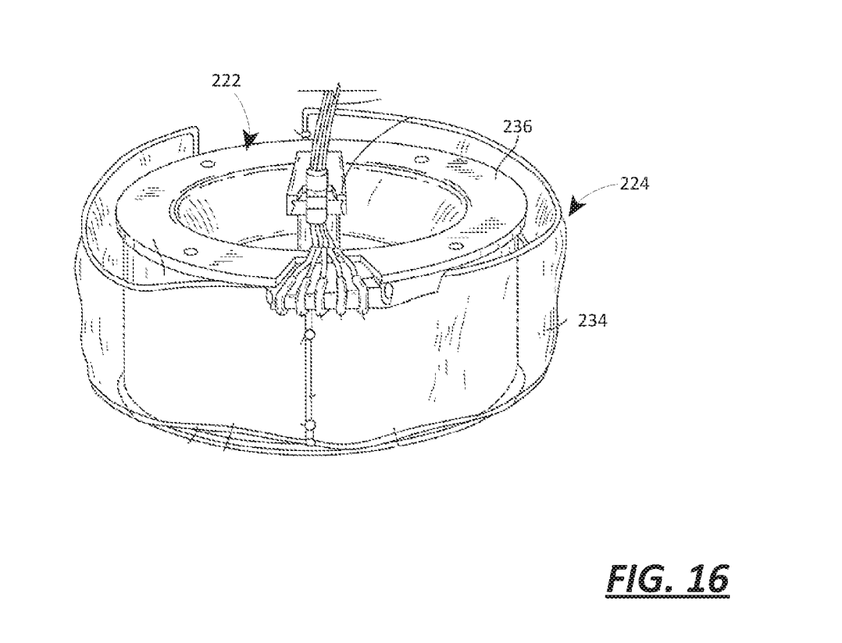
FIG. 16 is a schematic diagram of a sub-system of the reusable apparatus of FIG. 15.
Figure 17:
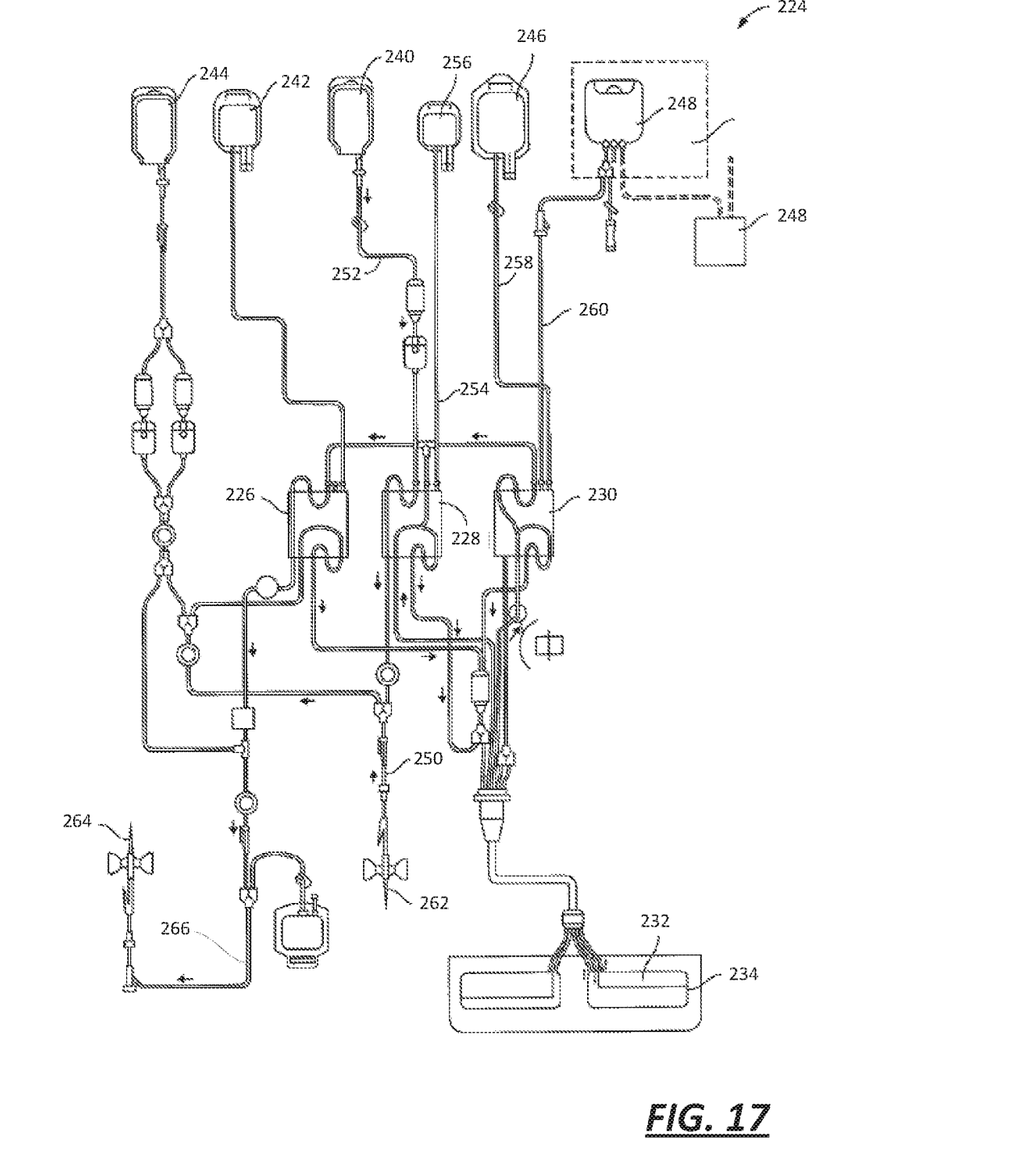
FIG. 17 is a schematic diagram of the disposable set of FIG. 15.

According to one embodiments of the medical system 200, the reusable device 204 may be an AMICUS® Separator, available from Fresenius Kabi USA, Lake Zurich, Illinoid, configured to carry out apheresis. Briefly, FIGS. 15-17 show such an embodiment of an apparatus 204, with FIG. 15 illustrating the structures of the apparatus 204 schematically, FIG. 16 illustrating a representative blood centrifuge (defining part of the cell separator 202) with a portion of a fluid circuit mounted thereon (which fluid circuit also may define part of the cell separator 202, and may be an embodiment of the fluid circuit 206), and FIG. 17 illustrating the remainder of the fluid circuit. Additional details of the interaction of such an apparatus and a set are discussed in U.S. Pat. No. 5,868,696, which is incorporated by reference herein in its entirety.

With reference first to FIG. 15, the illustrated embodiment of the apparatus 204 thus may include a controller 210, which may be configured as the controller 120 discussed above, and in particular may be configured to carry out one (or more) of the embodiments of the method discussed herein. The apparatus also includes an input device 212 in the form of a touch screen and an output device 214 in the form of an electronic display. The input devices 212 according to this embodiment may further include sensors (or sensor stations), such as weight scales, pressure sensors and air detectors. The controller 210 is coupled to the input devices 212 and the output device 214, as well as to a plurality of pumps 216 (e.g. peristaltic pumps), a plurality of valves (or valve stations) 218, and a centrifugal separator 222. Mounted on the pumps 216, the valves 218, and the separator 222 (which along with the sensors 212 may together define an embodiment of an interface) is a fluid circuit 224, which may be an embodiment of the fluid circuit 206. The controller 210 is configured (e.g., programmed) to control each of the pumps 216, valves 218, and the centrifugal separator 222 to carry out an instance of a procedure in combination with the fluid circuit 224.

Processing set (also referred to as a fluid circuit) 224 includes a plurality of processing fluid flow cassettes 226, 228, 230 (see FIG. 17) with tubing loops for association with peristaltic pumps 216. Set 224 also includes a network of tubing and connected (or pre-connected) containers for establishing flow communication with the patient and for processing and collecting fluids and blood and blood components, as discussed in detail below. The set 224 also includes a separation chamber 232.

As illustrated in FIGS. 16 and 17, the separation chamber 232 is defined by the walls of a flexible processing container 234 carried within an annular gap defined by a rotating spool element 236 (see FIG. 16) and an outer bowl element of the device. The processing container 234 takes the form of an elongated tube that is wrapped about the spool element 236 before use. The bowl and spool element 236 are pivoted on a yoke between an upright position and a suspended position. In operation, the centrifuge 222 rotates the suspended bowl and spool element 236 about an axis, creating a centrifugal field within the processing chamber 232 of container 234. Details of the mechanism for causing relative movement of the spool 236 and bowl elements as just described are disclosed in U.S. Pat. No. 5,360,542, the contents of which is also incorporated by reference herein in its entirety.

As seen in FIG. 17, the disposable processing set 224 may include the flexible processing container 234, as well as additional containers, such as a container 240 for supplying anticoagulant, a waste container 242 for collecting waste from one or more steps in a process, a container 244 for holding saline or other wash or resuspension medium, a container 246 for collecting plasma, as well as other containers 248. The set 224 also may include inlet line 250, an anticoagulant (AC) line 252 for delivering AC from container 240, an RBC line 254 for conveying red blood cells from chamber 232 of container 234 to a container 256, a platelet-poor plasma (PPP) line 258 for conveying PPP to container 246 and line 260 for conveying other fluids to and from separation chamber 232 and the containers 248. In addition, the blood processing set 224 includes one or more venipuncture needle(s) for accessing the circulatory system of the patient. As shown in FIG. 17, set 224 includes an inlet needle 262 attached to the inlet line 250 and a return needle 264 attached to a return line 266; in an alternative embodiment, a single needle can serve as both the inlet and outlet needle.

Fluid flow through set 224 is preferably driven, controlled and adjusted by the controller 210 in cooperation with the pumps 216, valves 218, and sensors 212, the details of which are described in the previously mentioned U.S. Pat. No. 5,868,696. In a general sense, blood is drawn from the patient via the inlet needle 262 into the inlet line 250, where it passes through one or more of the cassettes 226, 228, 230 and may be processed in the processing chamber 232. The containers 240, 242, 244, 246, 248, 256 are also connected via the cassettes 226, 228, 230 to the processing chamber 232, and fluids may be drawn from or passed to the containers 240, 242, 244, 246, 248, 256 as a consequence of the operation of the cassettes 226, 228, 230 and the chamber 232 (and associated pumps and spool/bowl element). Fluid is returned to the patient along return line 122 via return needle 264.

Other Aspects

Aspect 1. An irradiation device, comprising:
a processing container including a first chamber, a second chamber and at least one narrow passage in fluid communication at a first end with the first chamber and at a second end with the second chamber;
a rotatable table on which the processing container is mounted, the table having a first state wherein the first chamber is disposed at a higher elevation than the second chamber, and a second state wherein the second chamber is disposed at a higher elevation than the first chamber;
a UV light source disposed proximate to the narrow passage and configured to irradiate fluid passing through the narrow passage.

Aspect 2. The irradiation device according to aspect 1, wherein the first chamber has a curved wall that defines a first volume, the curved wall tapering to define the at least one narrow passage at least in part, and the second chamber has a curved wall that defines a second volume, the curved wall tapering to define the at least one narrow passage at least in part.

Aspect 3. The irradiation device according to aspect 1 or 2, wherein the container comprises a plurality of narrow passages in fluid communication at a first end with the first chamber and at a second end with the second chamber.

Aspect 4. The irradiation device according to aspect 3, wherein the container comprises:
a passage in fluid communication with the first chamber at a first end and the second chamber at the second end, the passage having a passage wall, and one or more baffles disposed in the passage to define the plurality of narrow passages between the one or more baffles and the passage wall.

Aspect 5. The irradiation device according to aspect 4, wherein the one or more baffles comprises a plurality of baffles, and at least one of the narrow passages is defined between two of the plurality of baffles.

Aspect 6. The irradiation device according to any one of aspects 1-5, wherein the first chamber has a different shape than the second chamber.

Aspect 7. The irradiation device according to any one of aspects 1-6, wherein the container has a longitudinal axis and a lateral axis, and the first and second chambers have a length in a direction of the longitudinal axis and a width in a direction of the lateral axis, and at least one of the length and the width of the first chamber is different than the at least one of the length and the width of the second chamber.

Aspect 8. The irradiation device according to any one of aspects 1-7, wherein the container comprises at least one port to permit fluid communication with the first chamber or the second chamber.

Aspect 9. The irradiation device according to any one of aspects 1-8, wherein the first chamber and the second chamber are disposed along a longitudinal axis of the processing container, and the table is rotatable about a table axis that is transverse to the longitudinal axis.

Aspect 10. The irradiation device according to aspect 9, wherein the table axis is orthogonal to the longitudinal axis.

Aspect 11. The irradiation device according to aspect 10, wherein the table has a table surface on which or to which the processing chamber is attached, and the table axis is orthogonal to the table surface.

Aspect 12. The irradiation device according to aspect 11, wherein the table revolves about the table axis to move the first and second chambers between the first and second states.

Aspect 13. The irradiation device according to any one of aspects 1-12, further comprising a motor attached to the table to rotate the table about the table axis.

Aspect 14. The irradiation device according to aspect 13, further comprising a controller coupled to the motor to actuate the motor to rotate the table about the table axis repeatedly between the first state and the second state and then between the second state and the first state.

Aspect 15. The irradiation device according to any one of aspects 1-14, wherein the UV light source comprises an array of UV light emitting diodes.

Aspect 16. A system for processing a biological fluid, the system comprising:
a cell separator configured to separate a biological fluid into at least two streams of cell components; and
an irradiation system according to any one of aspects 1-14, the processing container couplable to the cell separator to receive the cell components of at least one of the at least two streams.

Aspect 17. The system according to aspect 16, wherein the cell separator comprises a reusuable apparatus and a disposable fluid circuit mounted to or on the reusable apparatus, the fluid circuit couplable to the processing container.

Aspect 18. The system according to aspect 17, wherein the processing container is detachable from the fluid circuit.

The invention claimed is:

1. An irradiation device comprising:
a mountable processing container defining a first chamber and a second chamber separated by at least one narrow passage in fluid communication at a first end with the first chamber and at a second end with the second chamber; wherein the container has a longitudinal axis and a lateral axis, and the first and second chambers and said at least one narrow passage have a length in a direction of the longitudinal axis and a width in a direction of the lateral axis, and wherein the width of said at least one narrow passage is smaller than the width of said first and second chambers,
a rotatable table on which the processing container is mounted, the table having a first state wherein the first chamber is disposed at a higher elevation than the second chamber, and a second state wherein the second chamber is disposed at a higher elevation than the first chamber;
a single UV light source positioned over a portion of the rotatable table corresponding to the narrow passage, wherein the single UV light source is aligned with and proximate to the narrow passage and configured to only irradiate fluid flowing within the narrow passage,
wherein the narrow passage is defined by a portion of the container, the position of which is fixed between the first and second compartments; and
a controller configured to activate the single UV light source when fluid is flowing through the narrow passage.

2. The irradiation device according to claim 1, wherein the first chamber has a curved wall that defines a first volume, the curved wall tapering to define the at least one narrow passage at least in part, and the second chamber has a curved wall that defines a second volume, the curved wall tapering to define the at least one narrow passage at least in part.

3. The irradiation device according to claim 1, wherein the container comprises a plurality of narrow passages in fluid communication at a first end with the first chamber and at a second end with the second chamber.

4. The irradiation device according to claim 3, wherein the container comprises:
a passage in fluid communication with the first chamber at a first end and the second chamber at the second end, the passage having a passage wall, and one or more baffles disposed in the passage to define the plurality of narrow passages between the one or more baffles and the passage wall.

5. The irradiation device according to claim 4, wherein the one or more baffles comprises a plurality of baffles, and at least one of the narrow passages is defined between two of the plurality of baffles.

6. The irradiation device according to claim 1, wherein the first chamber has a different shape than the second chamber.

7. The irradiation device according to claim 1, wherein the container has a longitudinal axis and a lateral axis, and the first and second chambers have a length in a direction of the longitudinal axis and a width in a direction of the lateral axis, and at least one of the length and the width of the first chamber is different than the at least one of the length and the width of the second chamber.

8. The irradiation device according to claim 1, wherein the container comprises at least one port to permit fluid communication with the first chamber or the second chamber.

9. The irradiation device according to claim 1, wherein the first chamber and the second chamber are disposed along a longitudinal axis of the processing container, and the table is rotatable about a table axis that is transverse to the longitudinal axis.

10. The irradiation device according to claim 9, wherein the table axis is orthogonal to the longitudinal axis.

11. The irradiation device according to claim 10, wherein the table has a table surface on which or to which the processing container is attached, and the table axis is orthogonal to the table surface.

12. The irradiation device according to claim 11, wherein the table revolves about the table axis to move the first and second chambers between the first and second states.

13. The irradiation device according to claim 9, further comprising a motor attached to the table to rotate the table about the table axis.

14. The irradiation device according to claim 13, wherein the controller is coupled to the motor to actuate the motor to rotate the table about the table axis repeatedly between the first state and the second state and then between the second state and the first state.

15. The irradiation device according to claim 1, wherein the single UV light source comprises an array of UV light emitting diodes.

16. A system for processing a biological fluid, the system comprising:
  a cell separator configured to separate a biological fluid into at least two streams of cell components; and
  an irradiation system according to claim 1, the processing container couplable to the cell separator to receive the cell components of at least one of the at least two streams.

17. The system according to claim 16, wherein the cell separator comprises a reusable apparatus and a disposable fluid circuit mounted to or on the reusable apparatus, the fluid circuit couplable to the processing container.

18. The system according to claim 17, wherein the processing container is detachable from the fluid circuit.

* * * * *